US00PP21712P2

(12) United States Plant Patent
Wood

(10) Patent No.: US PP21,712 P2
(45) Date of Patent: Feb. 15, 2011

(54) ***SPIRAEA* PLANT NAMED 'GALEN'**
(50) Latin Name: *Spiraea japonica*
Varietal Denomination: Galen

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 10 days.

(21) Appl. No.: 12/583,682

(22) Filed: Aug. 25, 2009

(51) Int. Cl.
*A01H 5/00* (2006.01)

(52) U.S. Cl. ..... Plt./226
(58) Field of Classification Search ..... Plt./226

See application file for complete search history.

*Primary Examiner*—Wendy C Haas
(74) *Attorney, Agent, or Firm*—C. A. Whealy

(57) ABSTRACT

A new and distinct cultivar of *Spiraea* plant named 'Galen', characterized by its compact, upright, outwardly spreading and mounding plant habit; vigorous growth habit; freely branching habit; developing leaves that are dark burgundy in color that become green in color with development; numerous purple-colored flowers; good garden performance; and resistance to Powdery Mildew.

2 Drawing Sheets

Botanical designation: *Spiraea japonica.*
Cultivar denomination: 'GALEN'.

CROSS-REFERENCED TO RELATED APPLICATIONS

Applicant: Timothy D. Wood
Title: *Spiraea* Plant Named 'Yan'
Filed: U.S. Plant patent application Ser. No. 11/462,571

BACKGROUND OF THE INVENTION

The present invention relates to a new and distinct cultivar of *Spiraea* plant, botanically known as *Spiraea japonica* and hereinafter referred to by the name 'Galen'.

The new *Spiraea* plant is a product of a planned breeding program conducted by the Inventor in Grand Haven, Mich. The objective of the breeding program is to develop new compact *Spiraea* cultivars with strong foliage, large flowers and resistance to Powdery Mildew.

The new *Spiraea* plant originated from an open-pollination during the summer of 2004 of *Spiraea japonica* 'Walbuma', disclosed in U.S. Plant Pat. No. 9,363, as the female, or seed, parent with an unknown selection of *Spiraea japonica*, as the male, or pollen, parent. The new *Spiraea* plant was discovered and selected by the Inventor during the summer of 2006 as a single flowering plant within the progeny of the stated open-pollination in a controlled environment in Grand Haven, Mich.

Asexual reproduction of the new *Spiraea* plant by softwood cuttings in a controlled greenhouse environment in Grand Haven, Mich. since the summer of 2006 has shown that the unique features of this new *Spiraea* plant are stable and reproduced true to type in successive generations of asexual reproduction.

SUMMARY OF THE INVENTION

Plants of the new *Spiraea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Galen'. These characteristics in combination distinguish 'Galen' as a new and distinct cultivar of *Spiraea:*

1. Compact, upright, outwardly spreading and mounding plant habit.
2. Vigorous growth habit.
3. Freely branching habit.
4. Developing leaves that are dark burgundy in color that become green in color with development.
5. Numerous purple-colored flowers.
6. Good garden performance.
7. Resistance to Powdery Mildew.

Plants of the new *Spiraea* can be compared to plants of the female parent, 'Walbuma'. Plants of the new *Spiraea* differ from plants of 'Walbuma' in the following characteristics:

1. Plants of the new *Spiraea* are larger than plants of 'Walbuma'.
2. Plants of the new *Spiraea* and 'Walbuma' differ in leaf color as plants of 'Walbuma' have golden-colored leaves.
3. Plants of the new *Spiraea* have purple-colored flowers whereas plants of 'Walbuma' have pink-colored flowers.
4. Plants of the new *Spiraea* are more resistant to Powdery Mildew than plants of 'Walbuma'.

Plants of the new *Spiraea* can be compared to plants of the *Spiraea japonica* 'Yan', disclosed in U.S. Plant patent application Ser. No. 11/462,571. Plants of the new *Spiraea* differ from plants of 'Yan' in the following characteristics:

1. Plants of the new *Spiraea* are not as compact as plants of 'Yan'.
2. Plants of the new *Spiraea* and 'Yan' differ in leaf color.
3. Plants of the new *Spiraea* are more freely flowering than plants of 'Yan'.
4. Plants of the new *Spiraea* and 'Yan' differ in flower color as plants of 'Yan' have pink-colored flowers.

Plants of the new *Spiraea* can also be compared to plants of the *Spiraea japonica* 'Anthony Waterer', not patented. In side-by-side comparisons conducted in Grand Haven, Mich., plants of the new *Spiraea* differed from plants of 'Anthony Waterer' in the following characteristics:

1. Plants of the new *Spiraea* were shorter than plants of 'Anthony Waterer'.
2. Plants of the new *Spiraea* were more freely branching than plants of 'Anthony Waterer'.
3. Plants of the new *Spiraea* had purple-colored flowers whereas plants of 'Anthony Waterer' had violet pink-colored flowers.
4. Plants of the new *Spiraea* were more resistant to Powdery Mildew than plants of 'Anthony Waterer'.

BRIEF DESCRIPTION OF THE PHOTOGRAPHS

The accompanying colored photographs illustrate the overall appearance of the new *Spiraea* plant, showing the colors as true as it is reasonably possible to obtain in colored reproductions of this type. Colors in the photographs may differ slightly from the color values cited in the detailed botanical description which accurately describe the colors of the new *Spiraea* plant.

The photograph on the first sheet is a side perspective view of a typical plant of 'Galen' grown in a container.

The photograph on the second sheet is a close-up view of a typical inflorescence of 'Galen'.

DETAILED BOTANICAL DESCRIPTION

The aforementioned photographs and following observations, measurements and values describe plants of the new *Spiraea* grown in three-gallon containers in Grand Haven, Mich. during the spring and early summer in a polyethylene-covered greenhouse and under conditions which closely approximate commercial production. Plants were three years old when the photographs and the description were taken. In the description, color references are made to The Royal Horticultural Society Colour Chart, 1995 Edition, except where general terms of ordinary dictionary significance are used.

Botanical classification: *Spiraea japonica* 'Galen'.

Parentage:

*Female, or seed, parent.*—*Spiraea japonica* 'Walbuma', disclosed in U.S. Plant Pat. No. 9,363.

*Male, or pollen, parent.*—Unknown selection of *Spiraea japonica*, not patented.

Propagation:

*Type.*—By softwood cuttings.

*Time to initiate roots.*—About 15 days at 22° C.

*Time to produce a rooted young plant.*—About two months at 22° C.

*Root description.*—Fine to thick, fibrous; cream to brown in color.

*Rooting habit.*—Freely branching; dense.

Plant description:

*Plant form and growth habit.*—Perennial shrub; compact, upright, outwardly spreading and mounding plant habit; vigorous growth habit.

*Branching habit.*—Freely branching habit with about 20 primary lateral branches; pinching (removal of terminal apices) will enhance lateral branch development.

*Plant height.*—About 60 cm.

*Plant diameter* (*area of spread*).—About 80 cm.

Lateral branch description:

*Length.*—About 12 cm.

*Diameter.*—About 3 mm.

*Internode length.*—About 1.5 cm.

*Texture, developing.*—Slightly pubescent.

*Texture, developed.*—Woody.

*Color, developing.*—Close to 148D.

*Color, developed.*—Close to 165B.

Foliage description:

*Arrangement.*—Alternate or whorled, simple.

*Length.*—About 4.5 cm.

*Width.*—About 2 cm.

*Shape.*—Elliptic to ovate.

*Apex.*—Acute.

*Base.*—Cuneate.

*Margin.*—Doubly serrate.

*Texture, upper and lower surfaces.*—Smooth, glabrous.

*Venation pattern.*—Pinnate.

*Color.*—Developing leaves, upper surface: Close to 187A. Developing leaves, lower surface: Close to 187C. Fully expanded leaves, upper surface: Close to 146A; venation, close to 146A. Fully expanded leaves, lower surface: Close to 191A; venation, close to 146C.

*Petiole.*—Length: About 3 mm. Diameter: About 1 mm. Texture, upper and lower surfaces: Smooth, glabrous. Color, upper and lower surfaces: Close to 145A.

Flower description:

*Flower appearance/arrangement.*—Single rotate flowers arranged in compound corymbs; freely flowering habit with usually about 255 flowers per inflorescence; flowers face upright to outwardly.

*Natural flowering season.*—Continuous flowering from the late spring through the summer in Grand Haven, Mich.

*Fragrance.*—Faintly fragrant; sweet, pleasant.

*Inflorescence height.*—About 2.5 cm.

*Inflorescence diameter.*—About 4 cm.

*Flower diameter.*—About 5 mm.

*Flower length* (*height*).—About 5 mm.

*Flower bud.*—Length: About 2 mm. Diameter: About 2 mm. Shape: Globose. Color: Close to 166A.

*Petals.*—Quantity per flower: Single whorl of five. Length: About 2 mm. Width: About 2 mm. Shape: Orbicular. Apex: Obtuse to acute. Margin: Entire. Texture, upper and lower surfaces: Smooth, glabrous. Color: When opening, upper and lower surfaces: Close to 60C. Fully opened, upper surface: Close to 79C. Fully opened, lower surface: Close to 79D.

*Sepals.*—Quantity per flower: Single whorl of five. Length: About 1 mm. Width: About 1 mm. Shape: Rounded. Apex: Acute. Base: Truncate. Margin: Entire. Texture, upper and lower surfaces: Smooth, glabrous. Color: When opening, upper and lower surfaces: Close to 183B. Fully opened, upper and lower surfaces: Close to 139D.

*Peduncles.*—Length: About 1.7 cm. Diameter: About 1 mm. Strength: Strong. Texture: Smooth, glabrous. Color: Close to 145B.

*Pedicels.*—Length: About 3 mm. Diameter: About 0.5 mm. Strength: Strong. Texture: Smooth, glabrous. Color: Close to 145B.

*Reproductive organs.*—Androecium: Quantity per flower: About 25. Anther shape: Globose. Anther length: About 0.25 mm. Anther color: Close to 187A. Amount of pollen: Scarce. Pollen color: Close to 8D. Gynoecium: Quantity per flower: One. Pistil length: About 2 mm. Style length: About 1 mm. Style color:

Close to 60B. Stigma appearance: Globose. Stigma color: Close to 60B. Ovary color: Close to 145B.

*Seeds.*—Length: About 1 mm. Diameter: About 0.5 mm. Color: Close to 145A.

Garden performance: Plants of the new *Spiraea* have been observed to have good garden performance and to tolerate rain, wind and temperatures ranging from about −31C to about 38° C.

Pathogen/pest resistance: Plants of the new *Spiraea* have been observed to be resistant to Powdery Mildew. Plants of the new *Spiraea* have not been observed to be resistant to pests and other pathogens common to *Spiraea*.

It is claimed:

1. A new and distinct *Spiraea* plant named 'Galen' as illustrated and described.

* * * * *

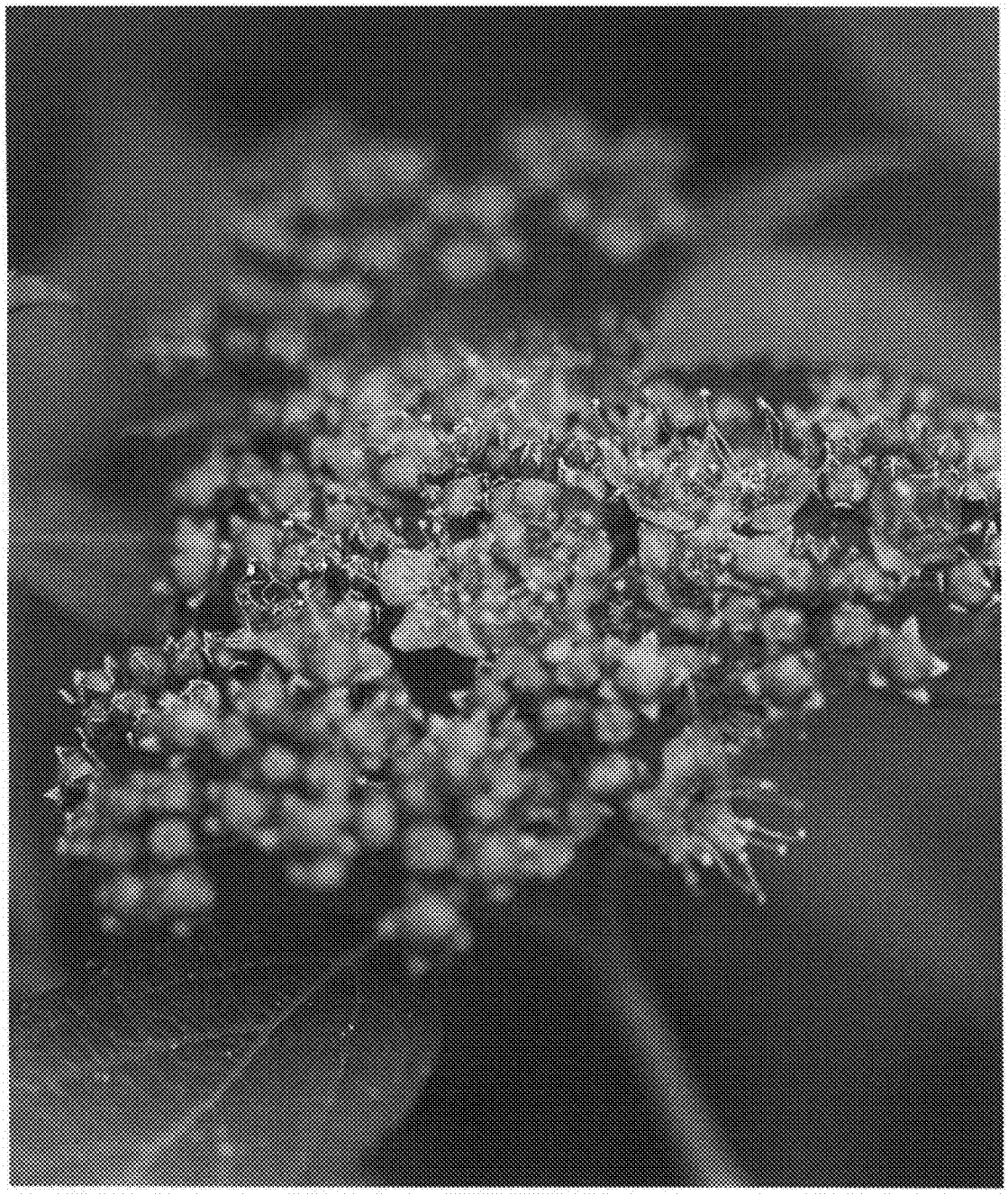

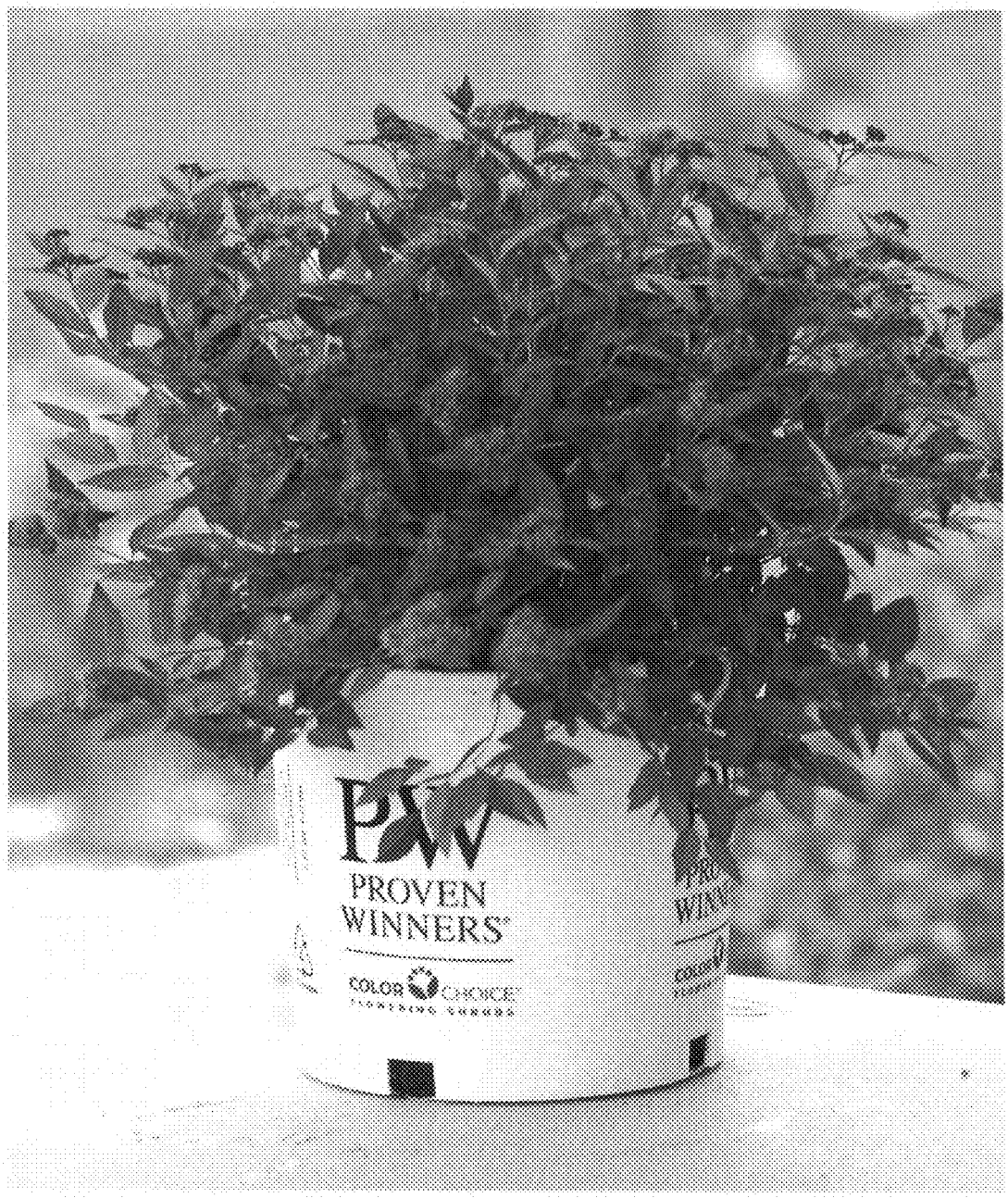
PW
PROVEN
WINNERS
COLOR CHOICE